United States Patent

Greco et al.

[11] Patent Number: 5,235,062
[45] Date of Patent: Aug. 10, 1993

[54] PROCEDURE FOR THE PREPARATION OF BISOXAZOLIDINES CONTAINING URETHANIC GROUPS

[75] Inventors: Alberto Greco, Dresano; Franco Mizia, San Donato Milanese; Franco Rivetti, Milan, all of Italy

[73] Assignee: Enichem Synthesis S.p.A., Palermo, Italy

[21] Appl. No.: 865,888

[22] Filed: Apr. 9, 1992

[30] Foreign Application Priority Data

Apr. 10, 1991 [IT] Italy .................. MI 91 A 000987

[51] Int. Cl.$^5$ ........................................... C07D 263/04
[52] U.S. Cl. .................................. 548/215; 548/216
[58] Field of Search .............................. 548/215, 216

[56] References Cited

U.S. PATENT DOCUMENTS

| | | | |
|---|---|---|---|
| 3,864,335 | 2/1975 | Emmons | 548/215 |
| 4,002,601 | 1/1977 | Hajek et al. | 548/215 |
| 4,138,545 | 2/1979 | Emmons et al. | 548/215 |
| 4,663,472 | 5/1987 | Green | 560/157 |

FOREIGN PATENT DOCUMENTS 0387926 9/1990 European Pat. Off. ............ 548/215
2286134 4/1976 France .

OTHER PUBLICATIONS

Adams et al. Chemical Review, pp. 567–601 (1965).

*Primary Examiner*—Donald G. Daus
*Attorney, Agent, or Firm*—Oblon, Spivak, McClelland, Maier & Neustadt

[57] ABSTRACT

New procedure for the preparation of polyoxazolidines which can be defined with the general formula:

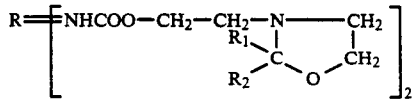

This procedure, which excludes the use of isocyanates, requires the simple transesterification of the dicarbamate of a diamine with an N-hydroxyalkyloxazolidine.

8 Claims, No Drawings

PROCEDURE FOR THE PREPARATION OF BISOXAZOLIDINES CONTAINING URETHANIC GROUPS

The present invention relates to a procedure for the preparation of polyoxazolidiens containing urethanic groups. These polyoxazolidines are useful as latent cross-linking agents in hygrohardening systems based on polyisocyanates, acrylate polymers and polyepoxides in compositions for coating, sealants and adhesives.

U.S. Pat. No. 3.743.626 describes the use of some polyoxazolidiens as hardeners, in atmospheric conditions of humidity and temperature, for adhesives based on both aromatic and aliphatic polyisocyanates. As it is described in U.S. Pat. No. 4.138.545, these polyoxazolidiens can be obtained by means of the reaction of an oxazolidien (A):

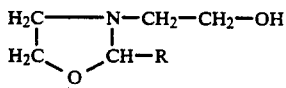

with lower alkyl esters of dicarboxylic or polycarboxylic acides, operating under transesterification conditions; or by means of the reaction of an oxazolidien (B):

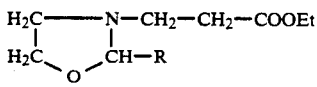

with a glycol or a polyol, again operating under transesterification conditions. The oxazolidines (B) are obtained by the addition of aldehydes to the addition product of ethanol amine and an alkylacrylate.

As the ester groups can be easily hydrolysed, the polyoxazolidines containing them and also the paints deriving from these, acquire a certain instability.

European Patent Application 228.935 describes the use of polyoxazolidines as cross-linking agents in normal conditions of humidity. These polyoxazolidines use bisalkanolamines (C) as starting products:

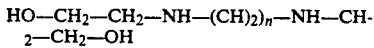

The synthesis of these alkanolamines, starting from amines and ethylene oxide, is not very selective. It is also necessary to separate these reaction products from the reaction mass, under conditions of high temperature and vacuum. Distillation is required because of the necessity of eliminating the tertiary amines (tri- and polyalkanolamines), which, if introduced into the polyisocyanate systems, reduce their duration owing to premature cross-linking, both chemically (alkanols) and catalytically (presence of tertiary nitrogen).

U.S. Pat. No. 4.296.225 describes the incorporation of polyoxazolidines as latent cross-linking systems, in polyvinyl systems, in the preparation of polyvinyl emulsions. In this case, the oxazolidine is introduced in the form of hydroxyalkyloxazolidine methacrylate, or as components in polyurethane paints with a high solid content. The principle is to introduce the oxazolidinic nucleus into a polyacrylate, which is made possible by using a vinyloxazolidine capable of copolymerizing in various degrees with the acrylic monomers. In all cases the oxazolidinic equivalent is not high and the polymers are excessively viscous solids or liquids, making it necessary to disperse them in water or dissolve them in an organic solvent.

In Italian Patent Application 19089 A/89 the same Applicant described a new group of polyoxaziolidines which can be used as cross-linking agents in systems based on polyisocyanates, acrylates or polyepoxides.

The main characteristic of these products is the presence of one or more thioether bridges in the structural formula, which, although giving stability to the photooxidation and a better oleoresistance to the manufactures into which these products are incorporated, generally have an unpleasant smell, which is typical of polysulphides. The same Applicant then described a new group of silanic compounds containing at least two oxazolidinic groups (Italian Patent Application 20189A/89) and in an Italian Patent Application has also described a new group of polyoxazolidines containing carbonate groups having excellent hydrolytic aging resistance. Finally, in Belgian Patent 833.821, Bayer has described the preparation of polyoxazolidines containing both urethane groups and a combination of isocyanate and urethane groups.

Urethane groups are extremely resistant to hydrolysis especially in an alkaline medium and consequently the final paints obtained starting from these compounds are very stable products. A further advantage of the presence of urethane groups in the polyoxazolidine, is the increased elasticity of the materials produced from them (paints etc.) and their resistance to abrasion.

The main disadvantage of their use is due to the proposed synthesis which contemplates the use of aliphatic and/or aromatic polyisocyanates, products which are notoriously dangerous, especially when inhaled.

The present invention relates to a procedure for the preparation of bisoxazolidines containing urethane groups which overcome the above draw-backs of the known art.

In particular, we have now found that it is possible to prepare bisoxazolidines containing urethane groups using a method which excludes the use of isocyanates in that it requires the simple transesterification of the dicarbamate of an aliphatic, cycloaliphatic or aromatic diamine with an N-hydroxyalkyloxazolidine, said carbamate being obtained without the use of isocyanates.

In accordance with this, the first aspect of the present invention relates to the preparation of bisoxazolidien, corresponding to the general formula (I):

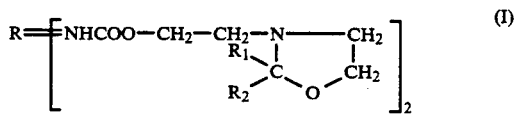

wherein R represents a bivalent radical of the alkylenic, linear or branched, cycloalkylenic type, which can be mono-, di-, tri and tetra-substituted with alkyl groups having a low number of carbon or arylenic atoms, $R_1$ and $R_2$, the same or different, represent the hydrogen atom, an alyl radical, with a linear or branched chain, containing from 1 to 6 carbon atoms, a cycloalkyl radical or an aryl radical, or, $R_1$ and $R_2$, taken together with the carbon atoms between them, represent a saturated cycloalkyl ring with 5, 6 or 7 carbon atoms, a procedure which is characterized by the reaction of N-hydroxyethyloxazolidien (II) with hedi-carbamate of a diuamine (III)

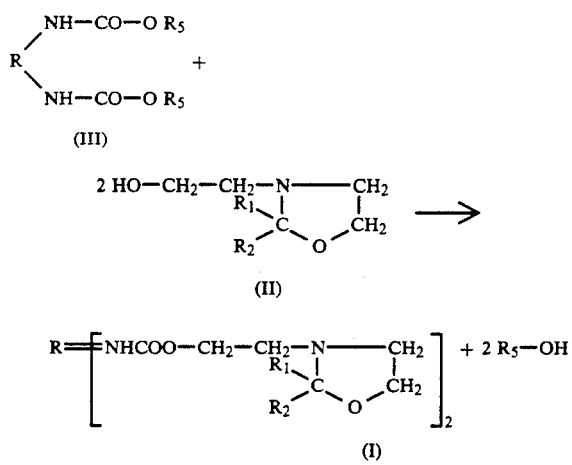

wherein $R_5$ represents an alkyl radical also unsaturated, linear or bran hea containing from 1 to 10 carbon atoms, a cycloalkyl radical which can also be substituted with one or more alyl groups or an aryl radical, whereas, R, $R_1$ and $R_2$ have the above mentioned meaning, in the presence of a transesterification catalyst and under such conditions of temperature and pressure as to enable the removal of the $R_5OH$ alcohols and phenols from the reaction medium by distillation as they are formed.

Examples of bivalent R radicals are the following: $(CH_2-)_m$ wherein m is an integer from 2 to 12,

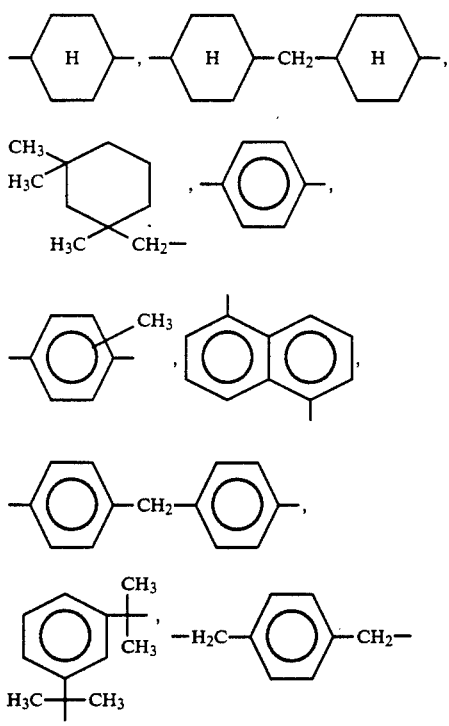

Examples of $R_5$ radicals are:- $CH_3$, Et, n-Pr, iPr, nBu, i-Bu, allyl, methallyl, phenyl etc.

More specifically, with reference to the above mentioned model, a carbamate corresponding to formula (III) is transesterified with a hydroxyethyloxazolidine corresponding to formula (II) in stoichiometric quantities or with a slight excess of (II) with respect to (III), at a temperature ranging from 60° to 140° C. and in the presence of a catalyst. The conditions should be such as to enable the $R_5OH$ alcohol (or phenol) to be easily removed by distillation as it is formed. Consequently if $R_5$ represents a particularly heavy group and therefore the $R_5OH$ alcohol has a particularly high boiling point, it may be necessary to resort to a partial vacuum.

In the presence of a suitable catalyst, the reaction between (II) and (III) to give I is easily started and is carried out at a temperature within the above range and with or without a partial vacuum until the stoichiometric quantity of $R_5OH$ has been collected.

The amine carbamate may also be formed in situ without being isolated (ex. 4) as the catalyst suitable for the formation of the amine carbamate is the same as the one used for the transesterification.

The presence of a solvent is not generally necessary even if in some cases it can be used to facilitate the removal of the $R_5OH$ alcohol during the transesterification. At the end of the reaction and when possible quantities of oxazolidine in excess have been removed by distillation under vacuum, the product obtained is cooled and the catalyst eliminated, using the conventional techniques for the catalytic system used.

If an excess of oxazolidine is used, the quantity should range from 1 to 50% in moles with respect to the stoichiometric quantity.

Either a sodium, lithium or potassium alcoholate of a low-boiling alcohol or an organometallic compound of $Sn^{II}$, $Sn^{IV}$, $Ti^{IV}$ or of other metals may be used as the transesterification catalyst; this preferably consists of sodium methylate.

The quantities of catalyst used vary from 50 to 1000 ppm with respect to the mixture of reagents.

If sodium methylate is used as catalyst, its removal at the end of the reaction involves neutralization with an organic or inorganic acid used in a stoichiometric quantity or a slight excess of the stoichiometry with respect to the sodium methylate. Any possible free acidity is removed by treatment with calcium oxide and subsequent filtration. When the catalyst is sodium methylate, the neutralizer is preferably p-toluenesulfonic acid, or phosphoric acid in a stoichiometric quantity or in slight excess with respect to the sodium methylate and preferably in the form of concentrated solutions in acetone, methylethylketone or another solvent.

The polyoxazolidine (I) is obtained with practically quantitative yields.

The advantage of polyoxazolidinic structures of the urethane type corresponding to formula (I) with respect to those of the polyester type of the known art is that the former give the end products a higher resistance to hydrolysis, better elasticity and abrasive resistance.

The bicarbamates corresponding to the structural formula (III) are products which are already known in the art as is also their preparation. They are generally prepared by reacting a $H_2H-R-NH_2$ diamine with a dialkyl- or diarylcarbonate in accordance with the following scheme:

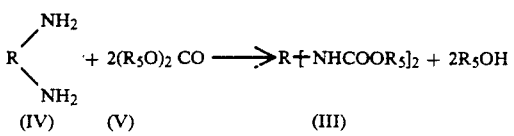

It is preferable to use dimethyl, diethyl, diallyl and diphenylcarbonate in that in the subsequent reaction of (III) with (II) an alcohol or phenol is released which can be easily removed from the reaction mass.

The reaction between the amines (IV) and carbonates (V) to give (III) is however part of the known art; it is fully described, for example, in the following documents:

1. Italian Patent Application 20042A/89
2. PCT Application WO 8805430
3. JP 02067261
4. U.S. No. 4.097.676
5. U.S. No. 3.443.019
6. U.S. No. 3.341.568
7. U.S. No. 4.395.565

The reaction is catalyzed, when alkyl carbonates such as dimethyl or diethylcarbonate are used, by Lewis acids or the alcoholates of alkaline or earth-alkaline metals. No catalyst is necessary when arylic carbonates such as diphenylcarbonate are used.

For example methyl hexamethylenedicarbamate $(CH_2)_6=\!\!=\!\!(NHCOOR_5)_2$ can be obtained by reacting the hexamethylenediamine added dropwise to the dimethylcarbonate in excess at $+60°-+70°$ C. under conditions of controlled temperature. This reaction is preferably carried out without a solvent, with about 3% in moles (with respect to the added amine) of sodium methylate as catalyst.

At the end of the reaction i.e. when the stoichiometric quantity of methyl alcohol has been reached, the catalyst is decomposed by treatment with phosphoric acid or p-toluenesulfonic acid in a stoichiometric quantity or by passing it over an acid resin bed, and the product is filtered in a boiler keeping it in its molten state after the excess unreacted dimethylcarbonate has been removed by distillation.

The hexamethylenediamine carbamate can be easily purified by recrystallization from the solvent but this is not generally necessary for the purposes of the this invention.

For the purposes of the present invention, the term "aryl radical" refers to a mono-, di-, or tri-cyclic radical containing from 6 to 14 carbon atoms, possibly substituted.

Similarly the term "arylenic radical" refers to an aromatic bivalent radical of the same type.

The procedure for the preparation of the polyoxazolidines (I) of the present invention has various advantages. First of all, the yield and selectivity values of the reactions involved are high. In addition, stable and manageable intermediates are used together with catalysts which can be easily removed; this makes possible to incorporate the polyoxazolidines of the present invention into the isocyanate systems without prejudicing the pot stability.

The polyoxazolidines (I) of the present invention are compatible with the most common groups of organic polymers and form latent cross-linking agents in that they hydrolyize immediately in the presence of humidity, even atmospheric humidity, with an opening of the oxazolidinic ring and generation of polyalkanolamines. They are therefore useful as cross-linking agents for polyisocyanates, polyepoxides and polyacrylates (Michael addition), in compositions for coatings, sealants and adhesives. These polyoxazolidines are particularly useful combined with polyisocyanates in that, owing to their intrinsic characteristics, they do not prejudice their duration, and can consquently be combined with said polyisocyanates in monocomponent systems, which are fluid under normal conditions, preferably without solvents and cross-linkable with atmospheric humidity without the formation of foam.

Suitable polyisocyanates for these formulations are those which can be obtained starting from aliphatic and/or aromatic isocyanates and from organic polymers, either difunctional or polyfuntional, with a low molecular weight (molecular weight of about 350–20,000), with a hydroxylic functionality at the chain-ends; or randomly distributed along the chain itself; among these are polyethers, polyesters, polycarbonates, polybutadienes and some hybrid polymers such as copolyether polycarbonate polymers and copolyester polycarbonate polymers with hydroxylic end-groups, and polyacrylates.

These polyisocyanates are mixed with the polyoxazolidines of the present invention in such a way that two equivalents of isocyanate groups in the polyisocyanate correspond to each oxazolidinic equivalent in the polyoxalidine. Variations in this stoichiometry are allowed, without excessive prejudice to the solidity of the cross-linked products, provided that the polyoxazolidine is present in quantities ranging from 30% defect to 10% excess with respect to the stoichiometric value.

The formulation between polyisocyanates and polyoxazolidines can be carried out at temperatures ranging from room temperature to 60° C., and is facilitated by the perfect compatibility between the two species involved. Suitable catalysts for accelerating the cross-linking may be used in the formulation, normally selected from metallic soaps, and in particular organometallic compounds of tin, and from organic acids, and in particular p-toluenesulfonic acid and benzoic or naphthoic acid. Apart from catalysts, other additives may be incorporated such as organic or inorganic charges, thixotropic agents, flame-resistant agents, adhesion promoters, stabilizers, U-V absorbers, in accordance with the conventional method.

The formulations thus obtained cross-link at a high rate, as a result of the atmospheric humidity, into end products having excellent general characteristics, especially in relation to thermal and chemical resistance and resistance to hydrolytic aging.

The experimental examples which follow provide a better illustration of the present invention.

EXAMPLE 1

Preparation of:

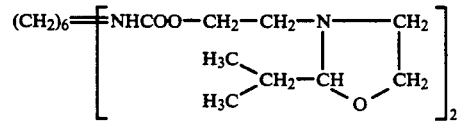

Hexamethylene 1,6 bis methylcarbamate (MW=232, g 348, 1.5 Moles) 2'hydroxy N ethenyl (2-isopropyl) 1,3 oxazolidine (g 540.8, moles 3.4), and a solution in methanol of sodium methylate (3ml, g 0.9 of $CH_3ONa$, moles 0.0167) are charged, in a nitrogen atmosphere, into a two litre 3-necked flask on which a distillation tower, equipped with an effective mechanical stirrer and nitrogen inlet, has been assembled.

The flask is immersed in an oil bath and its contents heated to $+110°$ C., the temperature at which the methanol begins to distil. To facilitate its removal a partial vacuum is applied, which slowly progresses to 50 mmHg and then to 1 mmHg, in accordance with the following table, the temperature in the tower being kept at +25 C.

| PRESSURE VARIATION | DURATION | DISTILLED LIQUID |
|---|---|---|
| 1st Phase normal pressure→50 mm Hg | 3 hrs | g 87 |
| 2nd Phase 50 mm Hg→1 mm Hg | 3 hrs | g 16 |
| | Total | g 103 |

Analysis of the distillate discloses methyl alcohol at 94% equal to g 96.5 of alcohol (100% of the theoretical value).

At this stage, the temperature of the boiler is brought to 120° C. and the one in the tower to 110° C. Over a period of 4 hours all the excess hydroxyethyloxazolidine distills (vacuum of 1 mmHg) (g 53.6; 0337 moles).

After the product is cooled to room temperature, p-toluenesulfonic acid is added (g 3.5, moles 0.0177) in methylethylketone (10 ml),k the addition being carried out dropwise under stirring. After stirring for 30' at r.t. CaO in powder form is added (10 g) and the product is stirred for one hour.

The product is then filtered in nitrogen on a G-2 orous glass septum equipped with a celite bed at a temperature of +75° c.

| Yield | g 732 (moles 1,506, 100%) |
|---|---|
| Appearance | transparent homogeneous |
| Colour | pale yellow |
| Viscosity | (+ 25° C.) 2600 cps. |
| Elemental analysis | C 58.62; H 9.67; N 11.23 |
| [theoretical values of $C_{24}H_{46}N_4O_6$; PM 486; C = 59.26, H = 9.47, N = 11.23] | |
| NMR spectrum: in accodance with the proposed structures. | |

EXAMPLE 2

Preparation of

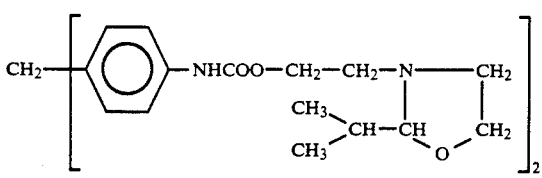

g.285 (moles 0.907) of

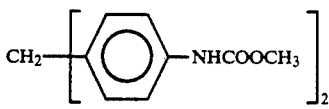

4,4 methylene bis [N-phenyl-O-methylcarbamate] transesterified with g 333.5 (moles 23.098) of N-hydroxyethyl-,23-isopropyl-1,3oxazolidien under the same conditions as described in example 1.

The quantity of light distillate (mainly methanol) is g 59.9, whereas the distailled N-hydroxyethyl-2-isopropyl-1,3-oxazolidien amounts to g 39.2 (70% of the theoretical value).

The product recovered in the flask is practically solid at room temperature, and consequently neutralization is carried out with p.luenesulfonic acid (g 3.5, moles 0.0177) in MEK (10 ml) at +50° C., the product is filtered (+110° c.) under the same conditions as described in Example 1.

| Yield | 518 (moles 0.907, 100%) |
|---|---|
| Appearance | transparent, homogeneous, semisolid |
| Colour | pale yellow |
| Viscosity | (+50° C.) 10600 cps |
| Elemental analysis | C = 65.05, H = 8.23, N = 9.70 |
| for a product with the formula $C_{31}H_{44}N_4O_6$ the following is required C = 65.49, H = 7.75, N = 9.86; PM 568) | |
| NMR spectrum in accordance with the proposed structures. | |

EXAMPLE 3

Isophorone bis [carbamoyl 2'N-ethenyl(3-isopropyl) 1,3 oxazolidine - 1,3 isphorone diamine bis methylcarbamate g 308, moles 1,075) and 2' hydroxy N ethenyl (2isopropyl) 1,3 oxazolidine (g 396, moles 2.365) were transesterified in the presence of NaMet (30% by weight in methanol, 6 ml) under the conditions described in example 1.

The light effluents were equal to g 62 (theoretical 68, 91%) and were composed of methanol; the heavy effluents, mainly composed (95%) of hydroxyethyloxazolidine, amounted to g 65 (0.38 moles; theoretical 60.5 g).

The semi-solid product at room temperature was heated to 50° C. and neutralized by adding phosphoric acid (g 3.60) in MEK (15 ml), and finally treated with CaO (10 g).

Filtration (+100° C.) gave g 598 of the product (100% yield).

| Appearance: | limpid, transparent, semi-solid |
|---|---|
| Viscosity (+50° C.): | 11,000 cps. |
| Elemental analysis: | C = 61.43, H = 46, N = 9.91 |
| | [$C_{28}H_{52}N_4O_6$, requires C = 62.22, H = 9.63, N = 10.37; PM 540] |
| | in conformance with the proposed structure. |

EXAMPLE 4

Anhydrous DMC (g 450.25, moles 5),hydroxyethyloxazolidine (g 334, moles 2.1) and sodium methylate (g 1.62, 5.4 ml of solution in $CH_3OH$) are charged into a flask equipped with a rectifying head, 10-plate column, with a drip-funnel, thermometer and stirrer with a mechanical blade.

The temperature is brought to +65° C. and hexamethylenediamine (g 116.2, one mole) is fed from the drip-funnel at such a rate as to keep the temperature at +65° C. (1 hour; the reaction is hexothermal).

At the end of the addition the reaction is kept at +65° C. for 2 hours after which the DMC is eliminated under vacuum and transesterification subsequently carried out at +65° C. for 6 hours, and under maximum vacuum.

The product in the boiler, after neutralization of the sodium methylate with p.toluenesulfonic acid, is treated with CaO and filtered (as in Example 1). It has the following characteristics:

| Colour: | pale yellow |
|---|---|
| Viscosity (cps, +25° C.): | 2700 |
| C = 58.9%; H = 9.38%; N = 11.32% | |

We claim:

1. Procedure for the preparation of bis-oxazolidiens corresponding to the formula (I)

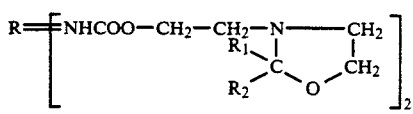
(I)

wherein R represents an alkylenic, linear or branched, cycloalkylenic, bivalent radical, which can be mono-, di- or tri-substituted with alkyl groups having a low number of carbon, or an aromatic biavlent radical, $R_1$ and $R_2$, the same or different, represent the hydrogen atom, an alkyl radical, with a linear or branched chain, containing from 1 to 6 carbon atoms, a cycloalkyl radical or an aryl radical or, $R_1$ or $r_2$, taken together with the carbon atoms between them, represent a saturated cycloalkyl ring with 5, 6 or 7 carbon atoms, comprising reacting N-hydroxyethyloxazolidine (II) with the dicarbamate of a diamine (III) according to the following equation:

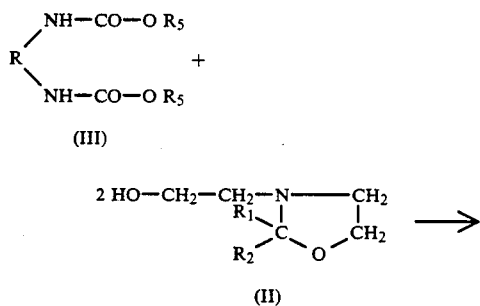

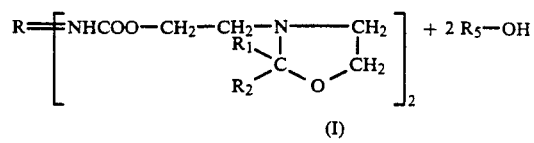
(I)

wherein R has the above mentioned meaning and $R_5$ represents an alkyl or unsaturated aliphatic radical, linear or branched, having from 1 to 10 carbon atoms, a cycloalkyl radical which can also be substituted with one or more alkyl groups or an aryl radical, and $R_1$ and $R_2$ have the above mentioned means, in the present of a sodium, lithium or potassium alcoholate transesterification catalyst and under such conditions of temperature and pressure as to allow the removal of the $R_5$ OH alcohols from the reaction medium by distillation as they are formed.

2. Procedure according to claim 1 wherein the transesterification temperature ranges from 60° C. to 140° C.

3. Procedure according to claim 1, wherein the transesterification temperature ranges from 80° C. to 120° C.

4. Procedure according to claim 1, wherein transesterification pressure ranges from atmospheric values to 0.1 mmHg.

5. Procedure according to claim 1, wherein the transesterification reaction is carried out in the presence of a solvent.

6. Procedure according to claim 1, wherein the transesterification reaction is carried out with an excess of from 1-50 mol% of hydroxyethyloxazolidine based on the stoichiometric quantity.

7. Procedure according to claim 1, wherein the transesterification catalyst is sodium methylate.

8. Procedure according to claim 1, wherein the quantities of catalyst used range from 50 to 1000 ppm with respect to the mixture of reagents.

* * * * *